(12) United States Patent
Park et al.

(10) Patent No.: US 9,933,403 B2
(45) Date of Patent: Apr. 3, 2018

(54) METHOD FOR ALARMING GAS AND ELECTRONIC DEVICE THEREOF

(71) Applicant: Samsung Electronics Co., Ltd., Gyeonggi-do (KR)

(72) Inventors: Daeun Park, Seoul (KR); Hyunkyoung Kim, Seoul (KR); Jihyun Ahn, Seoul (KR); Jung-Sik Park, Gyeonggi-do (KR); Hyung-Woo Shin, Seoul (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 0 days.

(21) Appl. No.: 15/143,723

(22) Filed: May 2, 2016

(65) Prior Publication Data
US 2016/0328947 A1 Nov. 10, 2016

(30) Foreign Application Priority Data

May 8, 2015 (KR) .................. 10-2015-0064579

(51) Int. Cl.
G08B 17/10 (2006.01)
G01N 33/00 (2006.01)
G08B 23/00 (2006.01)
H04M 1/725 (2006.01)

(52) U.S. Cl.
CPC ......... *G01N 33/0062* (2013.01); *G08B 23/00* (2013.01); *H04M 1/72522* (2013.01); *H04M 1/72572* (2013.01)

(58) Field of Classification Search
CPC .................. G01N 33/0062; G08B 23/00
USPC ........................................... 340/632
See application file for complete search history.

(56) References Cited

U.S. PATENT DOCUMENTS

| | | | |
|---|---|---|---|
| 2004/0056771 A1* | 3/2004 | Dungan | G01N 33/0075 340/632 |
| 2010/0050261 A1* | 2/2010 | Park | H04L 63/145 726/24 |
| 2014/0201182 A1* | 7/2014 | Amin | G06F 17/30477 707/706 |
| 2014/0305188 A1 | 10/2014 | Kume et al. | |

* cited by examiner

*Primary Examiner* — Kerri McNally
(74) *Attorney, Agent, or Firm* — Cha & Reiter, LLC

(57) ABSTRACT

A method for use in an electronic device, comprising: sensing a state of the electronic device; detect whether the state satisfies a predetermined condition; detecting a concentration of a gas in response to the state satisfying the predetermined condition; and displaying an indication of the concentration of the gas.

18 Claims, 21 Drawing Sheets

METHOD FOR ALARMING GAS AND ELECTRONIC DEVICE THEREOF

CLAIM OF PRIORITY

This application claims the priority under 35 U.S.C. § 119(a) to Korean Application Serial No. 10-2015-0064579, which was filed in the Korean Intellectual Property Office on May 8, 2015, the entire content of which is hereby incorporated by reference.

TECHNICAL FIELD

The present disclosure relates to electronic devices, in general, and more particularly to a method for alarming gas and electronic device thereof.

BACKGROUND

As digital technologies have developed, various types of electronic devices have become widely utilized, such as a mobile communication terminal, a smart phone, a tablet Personal Computer (PC), a Personal Digital Assistant (PDA), an electronic organizer, a notebook, a wearable device, or the like. The electronic device attains a mobile convergence step including the functions of other devices. For example, an electronic device may provide a call function such as a voice call, a video call and the like, a message transmit/receive function such as a Short Message Service (SMS)/Multimedia Message Service (MMS), an e-mail, and the like, an electronic organizer function, a photographing function, a broadcasting program reproduction function, a video reproduction function, a music reproduction function, an Internet function, a messenger function, a game function, a social network service (SNS) function, or the like.

The electronic device may include various types of sensors, and the electronic device may analyze a signal that is sensed by the sensors to perform various functions.

SUMMARY

According to aspects of the disclosure, a method for use in an electronic device is provided, comprising: sensing a state of the electronic device; detect whether the state satisfies a predetermined condition; detecting a concentration of a gas in response to the state satisfying the predetermined condition; and displaying an indication of the concentration of the gas.

An electronic device is provided comprising: a memory; a display; a gas sensor; and at least one processor operatively coupled to the memory, configured to: sense a state of the electronic device; detect whether the state satisfies a predetermined condition; detecting a concentration of a gas by using the gas sensor, in response to the state satisfying the predetermined condition; and displaying an indication of the concentration of the gas on the display.

BRIEF DESCRIPTION OF THE DRAWINGS

The above and other aspects, features, and advantages of the present disclosure will be more apparent from the following detailed description taken in conjunction with the accompanying drawings, in which.

DETAILED DESCRIPTION

Figure 1:
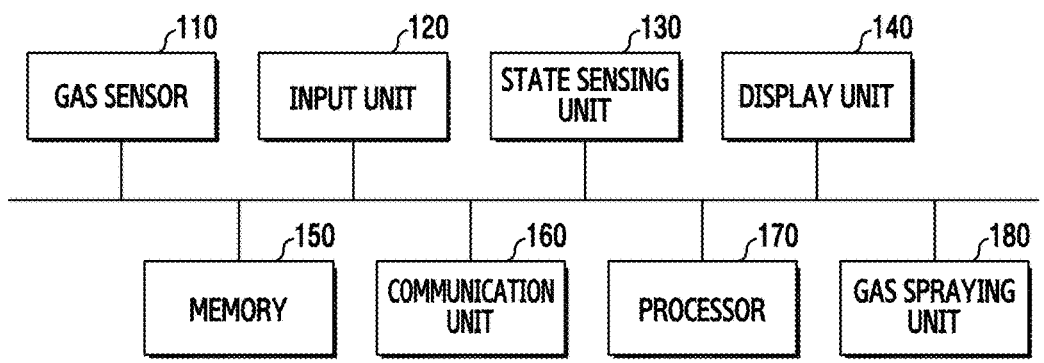
FIG. 1 is a diagram of an example of an electronic device, according to various embodiments of the present disclosure.

Hereinafter, various embodiments of the document will be described with reference to the accompanying drawings. However, it should be understood that there is no intent to limit the present disclosure to the particular forms disclosed herein; rather, the present disclosure should be construed to cover various modifications, equivalents, and/or alternatives to embodiments of the present disclosure. In describing the drawings, similar reference numerals may be used to designate similar constituent elements.

The terms used herein are merely for the purpose of describing particular embodiments and are not intended to limit the scope of other embodiments. As used herein, singular forms may include plural forms as well unless the context clearly indicates otherwise. Unless defined otherwise, all terms used herein, including technical and scientific terms, have the same meaning as those commonly understood by a person skilled in the art to which the present disclosure pertains. Such terms as those defined in a generally used dictionary may be interpreted to have the meanings equal to the contextual meanings in the relevant field of art, and are not to be interpreted to have ideal or excessively formal meanings unless clearly defined in the present disclosure. In some cases, even the term defined in the present disclosure should not be interpreted to exclude embodiments of the present disclosure.

An electronic device according to various embodiments of the present disclosure may include at least one of, for example, a smart phone, a tablet Personal Computer (PC), a mobile phone, a video phone, an electronic book reader (e-book reader), a desktop PC, a laptop PC, a netbook computer, a workstation, a server, a Personal Digital Assistant (PDA), a Portable Multimedia Player (PMP), a MPEG-1 audio layer-3 (MP3) player, a mobile medical device, a camera, and a wearable device. According to various embodiments, the wearable device may include at least one of an accessory type (e.g., a watch, a ring, a bracelet, an anklet, a necklace, a glasses, a contact lens, or a Head-Mounted Device (HMD)), a fabric or clothing integrated type (e.g., an electronic clothing), a body-mounted type (e.g., a skin pad, or tattoo), and a bio-implantable type (e.g., an implantable circuit).

In various embodiments of the present disclosure described in the below, the perspective of hardware is described as an example. However, various embodiments of the present disclosure include a technology that uses both hardware and software, and thus the various embodiments of the present disclosure may not exclude the perspective of software.

Many users who use an electronic device use air freshener products (e.g., perfume, air freshener, fiber deodorant, and the like). Also, the many users who use the electronic device normally use the air freshener products in regular intervals of time. However, the many users using the electronic device often forget using the air freshener products. In addition, although the time point when the air freshener products should be used occurs according to a change of the environment (e.g., change of temperature, weather and the like), the many users using the electronic device often cannot recognize this. Thus, an electronic device according to various embodiments of the present disclosure alarms a supplement time point of air freshener products to the user, thereby resolving these problems.

The many users using the electronic device may be located in an environment (e.g., a restroom, a construction site, a coal mine, and the like) in which a gas release is necessary. In addition, although the gas release is normally required in such an environment, the many users may not recognize this. Therefore, the electronic device according to various embodiments of the present disclosure outputs a message indicating a necessity of ventilation or controls to automatically drive an air cleaner, thereby resolving these problems.

FIG. 1 is a diagram of an example of an electronic device, according to various embodiments of the present disclosure.

Referring to FIG. 1, the electronic device 100 may include a gas sensor 110, an input unit 120, a state sensing unit 130, a display unit 140, a memory 150, a communication unit 160, a processor 170 and a gas spraying unit 180.

The gas sensor 110 may mean at least one gas sensor set. The gas sensor 110 may be densely positioned or widely positioned in the electronic device. The gas sensor 110 may sense a gas around the electronic device. Specifically, the gas sensor 110 may collect the gas around the electronic device, and may convert the collected gas into an electrical signal. The gas sensor 110 may be a semiconductor sensor.

The gas sensor 110 may be driven in a state of a predetermined condition to sense the gas. The state sensing unit 130 may sense the state of the predetermined condition. Here, the state of the predetermined condition may be at least one of a state releasing a security lock of the electronic device, a state sensing proximity of a user, a state sensing a touch of a device, and a state in which a device is moved to a configured specific position. Therefore, the gas sensor 110 may be driven to sense the gas when the state sensing unit 130 senses the state of the predetermined condition.

The input unit 120 may sense an input of the electronic device. The input unit 120 may be a touch panel. The input unit 120 may sense a touch of a finger and a pen, or a hovering input. The input unit 120 may generate inputs related to a gas sensing or processing according to various embodiments of the present disclosure.

The state sensing unit 130 may sense the state of the predetermined condition in which the gas sensor 110 may be driven in the electrode device. Here, the predetermined condition may be a generation of proximity or a contact between the electronic device and a user, and a movement of the electronic device to a configured position. The state sensing unit 130 may include a fingerprint recognizing sensor, a proximity sensor, a grip sensor, a geomagnetic sensor, an accelerometer, a gyroscope sensor, a g-sensor, a digital compass, a Global Navigation Satellite System (GNSS), and a camera.

The electronic device including the gas sensor 110 may sense a gas (e.g., perfume) generated from a user. In this case, the state sensing unit 130 may sense the gas in consideration of a condition of an access or a contact of the electronic device to a user, the position of the electronic device in a corresponding condition, and the like. In the configuration of such a condition, the following sensors may be used. The proximity sensor may be used in a sensing or a position control of an existence-or-not, a passage, a successive flow, an accumulation and the like of an object using power of an electromagnetic field without a physical contact. In addition, the proximity sensor may sense the distance between the user and the electronic device. The grip sensor is a sensor for sensing a grip when a user grips the electronic device using a hand or the like. The grip sensor may sense that a hand (e.g., a right hand or a left hand) grips the electronic device. The accelerometer may measure an acceleration or strength of a shock of a moving object. The gyroscope sensor may include each circulation function in the existing accelerometer and thus may recognize the total axes as six. The g-sensor may detect a direction in which gravity is applied.

When the electronic device enters into a specific area, the electronic device including the gas sensor 110 may sense a gas (e.g., scent) generated in a corresponding area. In this case, the state sensing unit 130 may sense the gas in consideration of a condition of an access or a position of the electronic device to or in a configured area, and the like. The configuration of such a condition, the following sensors may be used. The digital compass is a digitalized compass of a magnetic compass. The digital compass may recognize a bearing of north, south, east and west, like a normal compass, and may be used for the purpose of position information utilization. The GNSS may detect the position of the electronic device using a satellite. The GNSS may include at least one of a Global Positioning System (GPS), a Global Navigation Satellite System (Glonass), a Beidou Navigation Satellite System, a Galileo, and the European global satellite-based navigation system.

As described above, the state sensing unit 130 may sense whether the electronic device is close to the user using the above-mentioned components. In addition, the state sensing unit 130 may know whether the electronic device is being contacted by the user using the above-mentioned components. For example, the electronic device may recognize a proximity level between the electronic device and a face of the user using the state sensing unit 130 (specifically, the proximity sensor and the camera which are the elements of the state sensing unit 130). In addition, the electronic device may recognize whether the user is contacting the electronic device with a hand, and whether a specific body part of the user is close to the electronic device, using the state sensing unit 130 (specifically, the grip sensor and the proximity sensor of the state sensing unit 130). In addition, the electronic device may recognize whether the user is touching the electronic device with a finger or a pen using the state sensing unit 130 (specifically, the input unit 120). Also, the electronic device may recognize whether the user is touching a fingerprint recognizing unit of the electronic device using the state sensing unit 130 (specifically, the input unit 120 and the fingerprint recognizing sensor).

The electronic device may sense whether the electronic device is located in a specific position using the state sensing unit 130. For example, the electronic device may recognize the distance between the electronic device and a specific object A, and a direction of the electronic device using the state sensing unit 130 (specifically, the geo-magnetic sensor, the accelerometer, the gyroscope sensor, the g-sensor, the digital compass, and/or the GNSS).

The display unit 140 may display a process result of the electronic device. The display unit 140 may be a Liquid Crystal Display (LCD) or an Organic Light Emitting Diode (OLED). The display unit 140 may display a concentration of the sensed gas. In addition, the display unit 140 may display a message that identifies a corresponding state when the concentration of the sensed gas is out of a configured range.

The input unit 120 and the display unit 140 may be configured with an all-in-one touch screen.

The memory 150 may include any suitable type of volatile or non-volatile memory, such as Random-access Memory (RAM), Read-Only Memory (ROM), Network Accessible Storage (NAS), cloud storage, a Solid State Drive (SSD), etc. In operation, the memory 150 may store data sensed by the gas sensor 110. The memory 150 may store instructions, programs and the like associated with any module of the electronic device. In addition, the memory 150 may store a log of different concentration measurements that are taken by the electronic device.

The communication unit 160 may include various communication functions (e.g., LTE, Wi-Fi, Bluetooth, NFC and the like) for communication between the electronic device and an external system.

In addition, the communication unit 160 may be used for communication with an external server when information related to the gas sensed by the gas sensor 110 should be obtained.

In addition, the communication unit 160 may enable a communication between the electronic device and an external device. For example, the communication unit 160 may be connected to a network through a wireless communication or a wired communication to communicate with the external device. The communication unit 160 may transmit a gas release message (e.g., a gas spray message, a gas supplement message, a gas emission message, and the like) to the outside of the electronic device. In addition, the communication unit 160 may receive a message corresponding to the gas release message from the outside of the electronic device.

The processor 170 may include any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), etc. For example, in some implementations, the processor 170 may be implemented with a System on Chip (SoC). In addition, the processor 170 may be divided and may be combined with an internal element (e.g., the gas sensor, the state sensing unit and the like) of the electronic device, in case of need.

When the processor 170 identifies that the current state sensed by the state sensing unit 130 satisfies the predetermined condition, the processor 170 may drive the gas sensor 110. In addition, the processor 170 may include a function of analyzing and processing gas concentration measurements obtained by the gas sensor 110, a function of detecting the current state of the electronic device based on information detected by the state sensing unit, a function of controlling the display of the display unit 140, and the like.

Specifically, the processor 170 may perform the following functions.

When the state sensing unit 130 senses the current state of the electronic device, the processor 170 may check whether the sensed state is the predetermined condition. Here, the predetermined condition may be a state of the electronic device that is configured by a user when a gas is registered. Because a gas concentration may be changed according to a sense position. For example, a perfume concentration measured by the electronic device when a user holds the electronic device with a user's right hand and a perfume concentration measured by the electronic device when the user puts the electronic device in a user's trouser pocket may be different. In addition, when a concentration of a restroom air freshener is measured using the electronic device, the measured concentration may be changed according to the measurement position (e.g., a measurement of an inside of the restroom and a measurement of an outside of the restroom) of the electronic device. That is, the predetermined condition may be necessary for an accurate gas concentration measurement.

The processor 170 may detect the concentration of the gas by using the gas sensor 110. More particularly, the processor may obtain any suitable type of measure of gas concentration that is based on mass, volume, and the like. By way of example, the gas concentration measure may include one or more of a weight percent, molar concentration, molality, normality, volume percent and/or other calculating methods for measuring concentration.

The processor 170 may determine whether the detected concentration is within a predetermined range. Here, the configured range may be a concentration range of a gas defined by a user. For example, when the configured range of gas A is 20 to 40% and a measured concentration of the gas A is 25%, the processor 170 may determine that the detected concentration of gas A is within the predetermined range.

The processor 170 may the detected concentration in the memory 150 in a time log. The time log may identify different measured concentrations and the times at which each of the concentrations is measured.

The processor 170 may measure an average concentration for a given time period using the concentration data stored in the time log. For example, when the concentration of the gas A at 2 P.M. is measured to 20% in the first day, measured to 30% in the second day, measured to 40% in the third day, measured to 30% in the fourth day, and is measured to 20% in the fifth day, the processor 170 may measure the average concentration of the gas A to 28% (i.e., (20+30+40+30+20)/5%). The above example may be just one example for calculating the average concentration. The processor 170 may measure the average concentration by other calculation methods if a method of using the log data is maintained.

The processor 170 may measure an average gas change in a given time period. For example, when the average concentration of the gas A is 50% at 2 P.M., 35% at 3 P.M., and is 10% at 4 P.M., the electronic device may measure the gas change amount between 2 P.M. and 3 P.M. to be 15%, and may measure the gas change amount between 3 P.M. and 4 P.M. to be 25%. The above example may be just one example for calculating the gas change amount per time. The processor 170 may measure the gas change amount per time by other calculation methods if a method of using the log data is maintained.

The processor 170 may specify a gas release message display time using the gas change amount per time. In the above example, when the current gas concentration of the gas A measured at 2 P.M. is 40%, the processor 170 may control the display unit 140 to display the gas release message at 4 P.M.

The processor 170 may control the display unit 140. The processor 170 may control the display unit 140 to display the concentration of the sensed gas based on the measured average concentration per time. For example, when the measured average concentration per time is 50% and the concentration of the sensed gas is 20%, the electronic device may display a sensing of the gas of 40% (i.e., 20% (i.e., the concentration of the sensed gas)/50% (i.e., the measured average concentration per time)) differently from a normal case. In addition, the processor 170 may control the display unit 140 to display the gas release message when the concentration of the sensed gas is out of a specific range. For example, when the specific range is 20 to 40% and the measured gas concentration is 10% or 50%, the processor 170 may control the display unit 140 to display the gas release message.

The processor 170 may control the communication unit 160. When the gas release is necessary, the processor 170 may control the communication unit 160 to transmit the gas spray or charge instruction to the outside of the electronic device. In addition, when a feedback corresponding to the transmission is received through the communication unit 160, the processor 170 may perform a process according to this.

The gas spraying unit 180 is a device capable of storing and releasing the gas. In addition, the gas spraying unit 180 may include a gas processing unit that processes the gas storage, an electrical signal storing unit of the sensed gas, a cartridge including gas components, a spraying unit that sprays the gas, and the like. The gas spraying unit 180 may be positioned inside the electronic device. The gas spraying unit 180 may be positioned outside the electronic device, and may be connected to the electronic device through a communication. Although in the present example the gas spraying unit 180 is used, in some implementations any suitable type device that is capable of releasing gas can be used instead.

When the spray or supplement of the gas is necessary as a result of the measurement by the processor 170, the gas spraying unit 180 may perform the spray or supplement of the gas. The gas spraying unit 180 may be positioned inside the electronic device. The gas spraying unit 180 may be positioned outside the electronic device, and may be connected to the electronic device through a communication. A method of communication may be a wired communication or a wireless communication. When the gas spraying unit 180 is positioned outside of the electronic device, the gas spraying unit 180 may include a transmitter/receiver, a communication module, and the like required to perform the communication.

Figure 2:
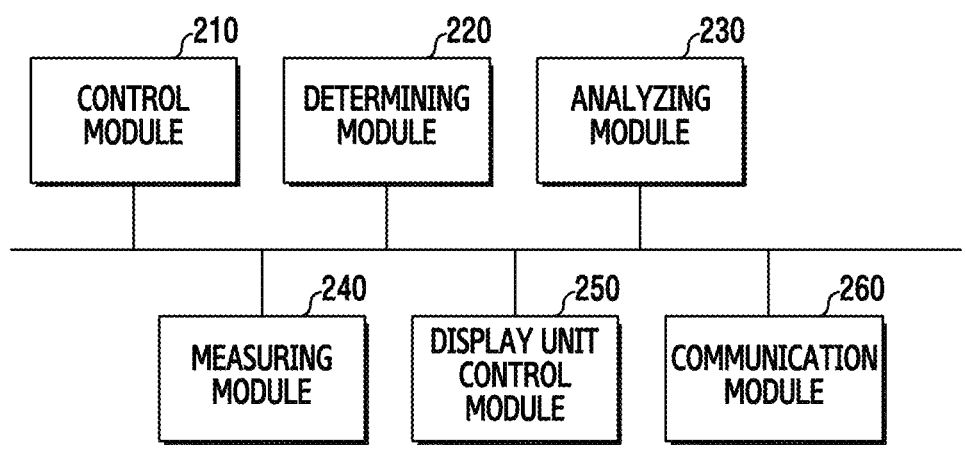
FIG. 2 is a diagram of an example of a processor configuration, according to various embodiments of the present disclosure.

FIG. 2 is a diagram of an example of a processor configuration, according to various embodiments of the present disclosure. As illustrated, the processor 170 may include a control module 210, a determining module 220, an analyzing module 230, a measuring module 240, a display control module 250, and a communication module 260. Any of the modules 210-260 may be implemented in hardware, software, and/or a combination of hardware and software.

The control module 210 may control the overall operations of elements (e.g., the gas sensor 110, the input unit 120, the state sensing unit 130, the memory 150, and the like) inside the electronic device.

The determining module 220 may determine whether the current state of the electronic device that is sensed by the state sensing unit 130 corresponds to the predetermined condition. When the current state of the electronic device corresponds to the predetermined condition, the determining module 220 may control the gas sensor 110 to sense the gas. In addition, the determining module 220 may determine whether the concentration detected by the electronic device is out of the configured range. In addition, the determining module 220 may determine whether the gas release message display time is elapsed, using the gas change amount per time measured by the processor 170.

The analyzing module 230 may detect the concentration of the gas sensed by the gas sensor 110. The concentration data for the concentration detected by the analyzing module 230 may be stored in the memory 150 according to a control of the control module 210.

The measuring module 240 may measure the average concentration for a given time period by using the concentration data for the detected concentration. The measured average concentration for a given time period may be a reference concentration when the measured concentration is displayed on the display unit 140. In addition, the measuring module 240 may measure the average gas change amount per time using the measured average concentration. The average gas change amount per time may be a value specifying the display time of the gas release message.

The display control module 250 may include a Graphic Processing Unit (GPU) and/or an image signal processor. The display control module 250 may control to display the gas concentration detected by the analyzing module 230, and/or the average concentration measured by the measuring module, on the display unit 140. In addition, the display control module 250 may control the display unit 140 to display the gas release message on the display unit 140 when the detected gas concentration is out of a specific range or the time specified as the gas release message display time has arrived. Also, the display control module 250 may control the display unit 140 to display the detected gas concentration on the display unit 140 such that the measured average concentration corresponds to a reference concentration.

The communication module 260 may perform a function of controlling the communication unit 160. When the gas spray or the gas charge is necessary, the communication module 260 may control the communication unit 160 to transmit the gas spray message or the gas charge message.

As described above, the electronic device according to various embodiments of the present disclosure may include the state sensing unit 130 which senses the state of the electronic device, the gas sensor 110 which senses the gas if the sensed state satisfies the predetermined condition, the processor 170 which detects the concentration of the sensed gas, and the display unit 140 which displays the concentration.

The display unit 140 may display a message which informs of the supplement of the gas if the concentration of the gas is out of the configured range. In addition, if the electronic device is in a standby mode, the display unit 140 may display the gas concentration on a standby screen. Also, if the electronic device is in an active mode, the display unit 140 may display the concentration on an indicator screen.

In addition, the electronic device may store concentration data (e.g., one or more concentration measurements) in the memory 150. The processor 170 may calculate the average concentration based on the concentration data if the number of concentration measurements that are part of the concentration data is equal to or larger than a reference number. The display unit 140 may display the detected gas concentration corresponding to the average concentration.

Also, the memory 150 may store the concentration data (e.g., gas concentration measurements) in a time log identifying the concentration of the gas that is measured at different time instants. The processor 170 may measure average concentration according to the contents of the time log if the number of measurements present in the time log is equal to or larger than the reference number.

In the state of the electronic device, the predetermined condition may be a case in which a user is close to the electronic device or a case in which a user makes contact with the electronic device. In this case, the gas sensed by the electronic device may be a perfume. In addition, the predetermined condition in the state of the electronic device may be a case in which the electronic device moves to a configured position.

Also, the electronic device may perform an operation of driving the gas sensor if the electronic device releases a security lock, and may perform an operation of turning off the gas sensor if the electronic device operates the security lock.

The electronic device according to various embodiments of the present disclosure may perform the following operations.

According to an embodiment, when the current state of the electronic device sensed by the state sensing unit corresponds to the predetermined condition, the electronic device may collect the gas through the gas sensor 110. At this time, the collected gas may accumulate the log data in the memory 150 under the control of the processor 170.

According to an embodiment, the electronic device may register the gas. The gas registration may be divided into a manual registration and an automatic registration. In the case of the manual registration, a user of the electronic device may register the gas in the electronic device in a method in which the user directly sprays the gas to the electronic device and registers the gas name. In the case of the automatic registration, the electronic device may collect a peripheral gas in a specific situation, and may register the gas when the collected gas is not registered in the electronic device. The electronic device may register a plurality of gasses in case of need.

According to an embodiment, the electronic device may sense the gas (e.g., a gas component of a perfume, and the like). The electronic device may sense the gas when the state of the predetermined condition is sensed, or may sense the gas in a regular time interval. In addition, the predetermined condition may be a time point (e.g., a time point when the electronic device recognizes that a user is close to the electronic device through a proximity sensor, or a time point when the user releases the security lock and a finger of the user or a pen for the electronic device contacts to the electronic device) determined as a time point when the user uses the electronic device, and the like.

According to an embodiment, the electronic device may accumulate and analyze the log data of the user. The electronic device may detect the average concentration data of the gas which is optimized to the user. The electronic device may accumulate the concentration data of the gas according to a time, while the user uses the electronic device. Also, when n concentration measurements are accumulated (e.g., wherein n can be any positive integer greater than 1), the electronic device may calculate an average value of the concentration of the gas optimized to a user's environment according to a use time. The electronic device may detect a time when the users charges the gas. The electronic device may measure and accumulate a time when the concentration of the gas registered by the user is the highest to draw a regular cycle of the gas use by the user. The electronic device may accumulate the data by dividing the data according to a type of the gas, in case of need.

Figure 3:
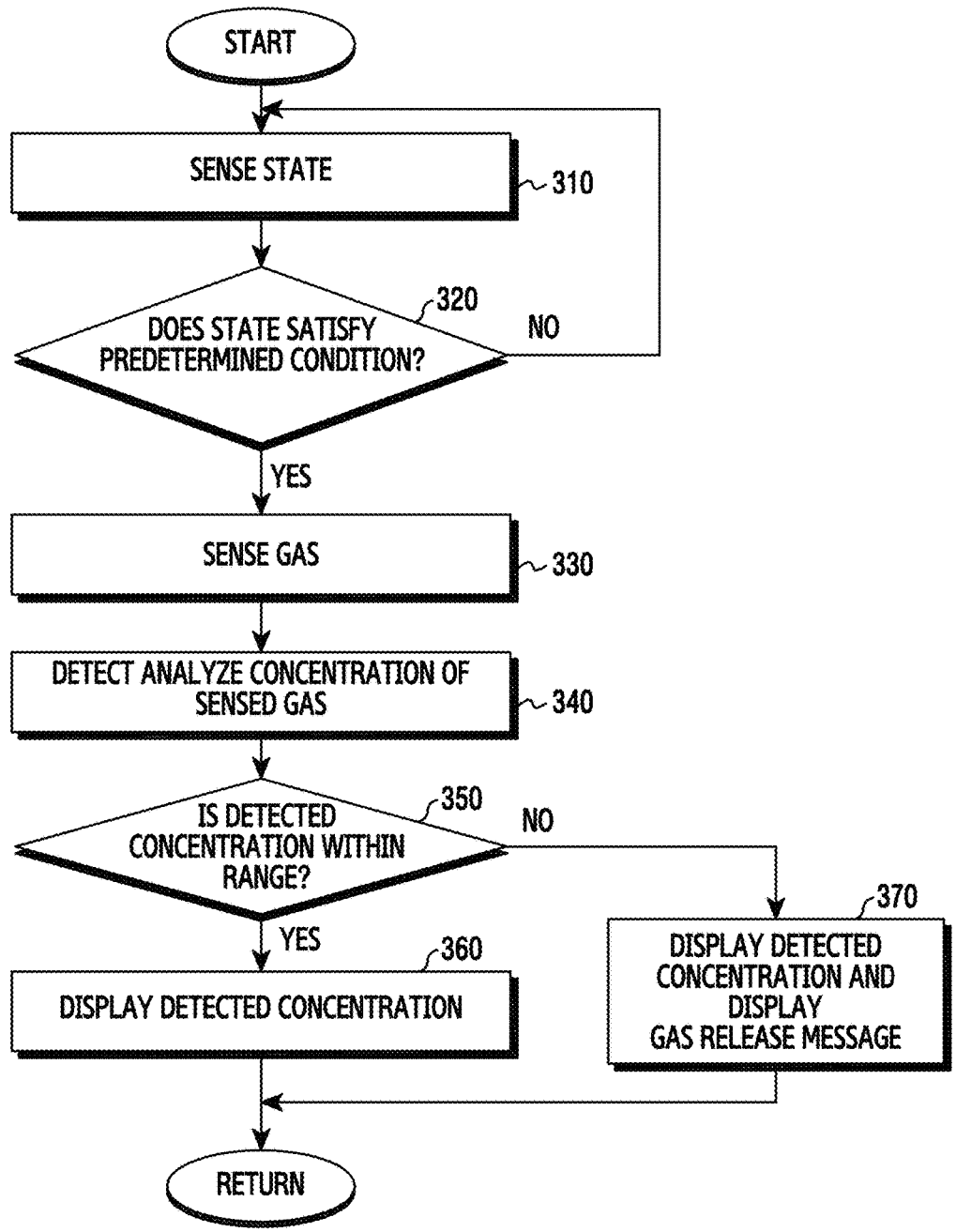
FIG. 3 is a flowchart of an example of a process, according to various embodiments of the present disclosure.

According to an embodiment, the electronic device may provide the gas concentration to a user. The electronic device may measure the concentration of the gas, and may display the concentration of the gas on the display unit 140 such that the user knows the concentration of the gas. In addition, when the plurality of gasses is registered, the electronic device may provide divided displays for each of the plurality of gasses. Also, the electronic device may provide a display based on an average value of the concentration of the gas used by a user. That is, the electronic device may calculate the average value of the concentration of the gas optimized to the user, and may provide the display according to a ratio of the average value rather than an absolute value of the concentration of the gas. When the measured gas concentration is 0% or is out of a predetermined range, or the gas release time point has arrived, the electronic device may provide an alarm (or alert) to a user. The user may charge the gas again according to the alarm. In addition, the electronic device may directly charge or spray the gas by controlling the gas spraying unit 180 together with the alarm. Furthermore, the electronic device may draw the gas use cycle of the user through the measurement of the time when the gas concentration is the highest, and may provide the alarm through the gas use cycle. FIG. 3 is a flowchart of an example of a process, according to various embodiments of the present disclosure. According to the process, in step 310, the electronic device may sense the current state of the electronic device. When the electronic device is in a state satisfying a condition specified by a user or the electronic device enters into the configured area, the electronic device may perform the gas sensing operation. In step 310, the electronic device may sense whether the electronic device is in the state of the predetermined condition (e.g., whether the electronic device is being contacted by a user, whether the electronic device is close to the user, or whether the electronic device is placed in a specific area) through the state sensing unit 130.

When the current state of the electronic device is sensed, in step 320, the electronic device may determine whether the current state of the electronic device satisfies a predetermined condition. As is discussed further below, the predetermined condition may be satisfied when the user grips or otherwise touches the electronic device. Additionally or alternatively, the condition may be satisfied when the user interacts with the electronic device in a given manner. Additionally or alternatively, the predetermined condition may be satisfied when the electronic device is located in a specific area (e.g., geographic area).

When the state of the electronic device does not satisfy the predetermined condition, in step 320, the process may return to operation 310. However, when the current state of the electronic device corresponds to the predetermined condition, in step 330, the electronic device may drive the gas sensor 110 to sense the gas.

In addition, in step 340, the electronic device may detect the concentration of the sensed gas. When the concentration is detected, in step 350, the electronic device may determine whether the detected concentration is within a predetermined range. For example, the predetermined range may be a value designated by a user. In addition, the range may have only an upper limit, may have only a lower limit, or may have both of the upper limit and the lower limit. When it is determined that the detected concentration is within the predetermined range in step 350, the electronic device may identify this in step 350. In step 360, the electronic device may display the detected concentration of the gas on the display unit 140. However, when the detected concentration is out of the predetermined range (e.g., when the detected concentration is higher than the upper limit of the range or is less than the lower limit of the range), in step 370, the electronic device may display the detected concentration of the gas, and may display the gas release message such that the gas of the predetermined range is maintained. The gas release message may be configured with a display method capable of arousing the caution of a user, a method of generating a sound (e.g., alert and the like) using a speaker or other devices, or a method by a combination thereof.

Figure 4:
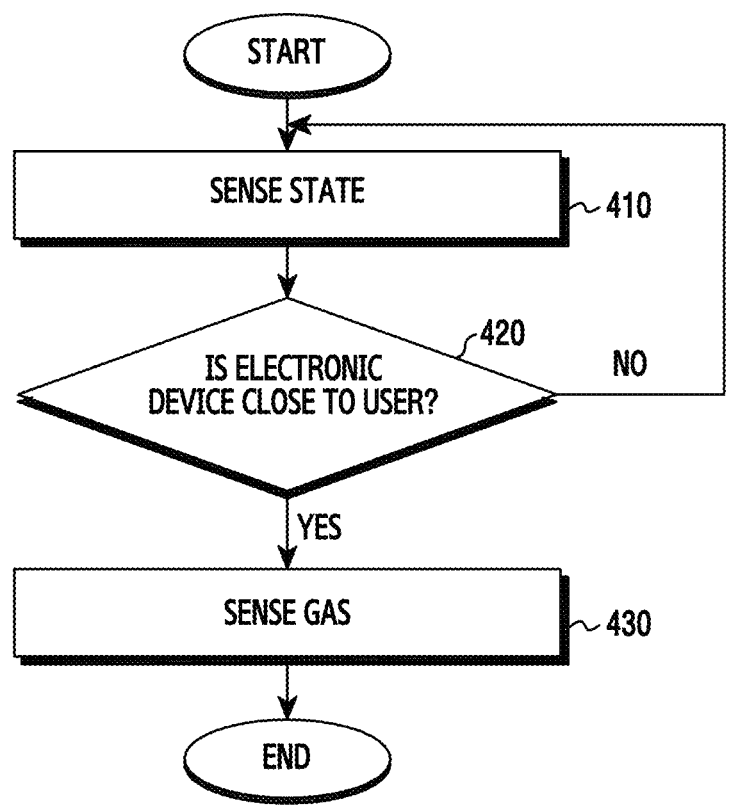
FIG. 4 is a flowchart of an example of a process, according to various embodiments of the present disclosure.
Figure 5:
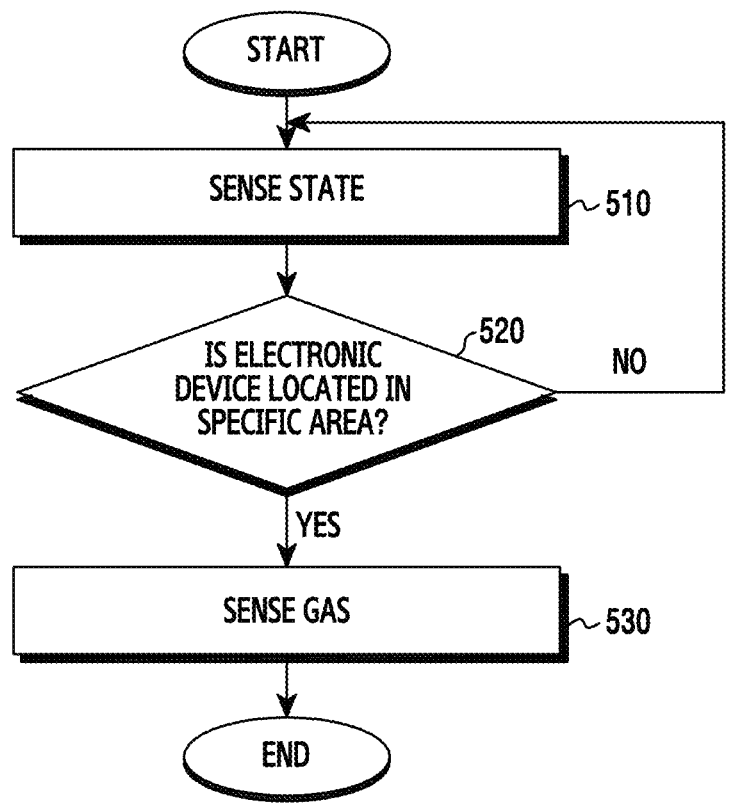
FIG. 5 is a flowchart of an example of a process, according to various embodiments of the present disclosure.

FIGS. 4 and 5 are flowcharts of processes for performing a sensing operation, according to various embodiments of the present disclosure. More specifically, FIG. 4 illustrates a gas sensing operation when a specific body part of the user is close to the electronic device or is contacted with the electronic device according to various embodiments of the present disclosure. FIG. 5 illustrates a gas sensing operation when the electronic device is positioned in a predetermined area according to various embodiments of the present disclosure. The operation procedure shown in FIGS. 4 and 5 may be controlled by the processor 170 of FIG. 1.

Figure 6A:
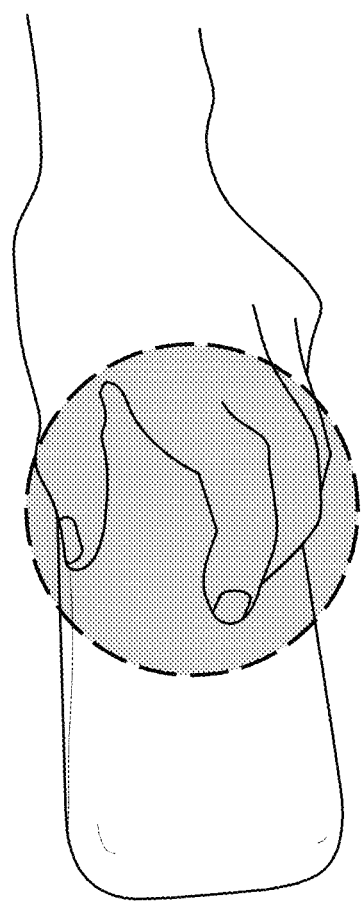
FIG. 6A is a diagram illustrating the operation of an electronic device, according to various embodiments of the present disclosure.
Figure 6B:
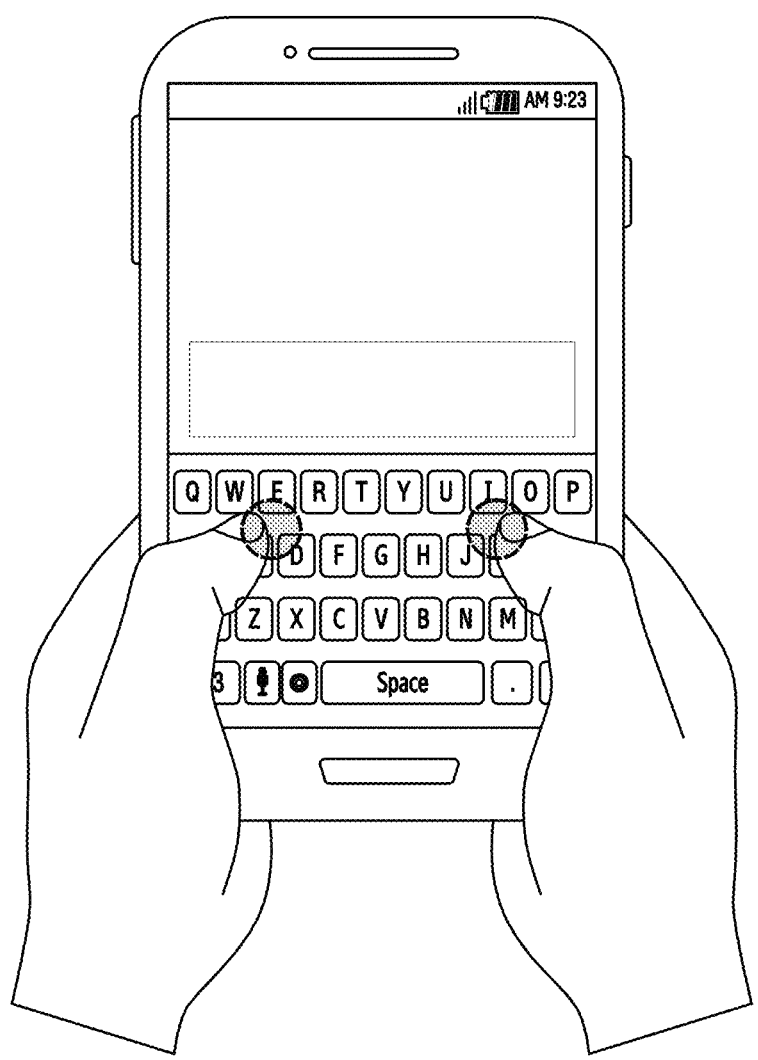
FIG. 6B is a diagram illustrating the operation of an electronic device, according to various embodiments of the present disclosure.
Figure 6C:
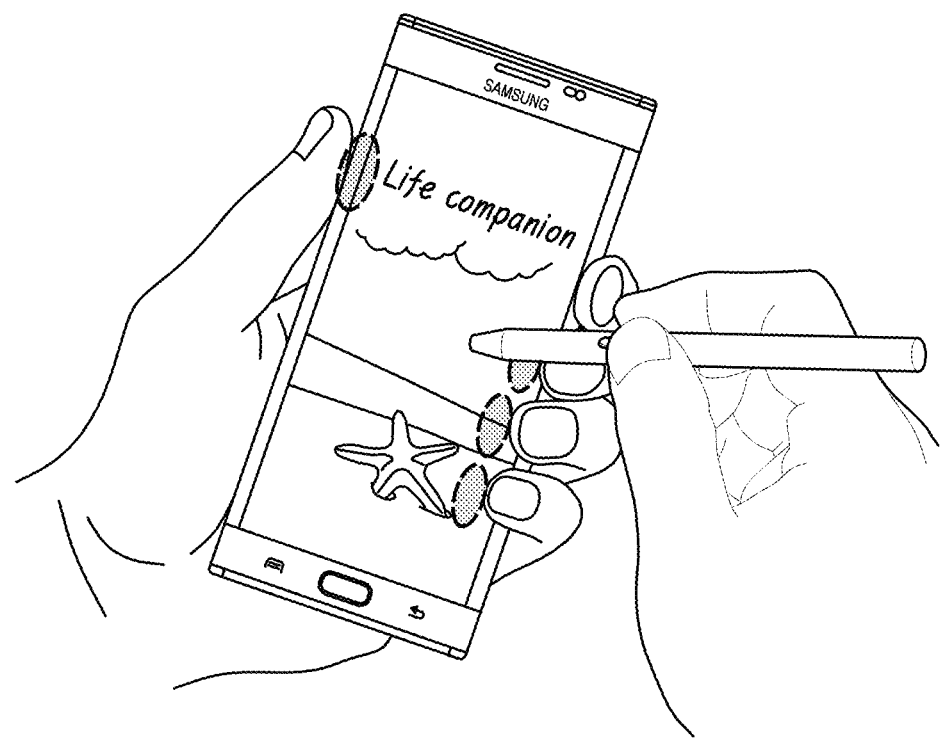
FIG. 6C is a diagram illustrating the operation of an electronic device, according to various embodiments of the present disclosure.

FIGS. 6A to 6C are diagrams illustrating the operation of an electronic device, according to various embodiments of the present disclosure.

Referring to FIG. 4, in step 410, the electronic device may sense its state through the state sensing unit 130. When the electronic device senses a scent of a user, the electronic device may configure a state in which the electronic device makes contact with the user or is accessed to the user as a gas sensing condition. The sensed condition may be satisfied when the user grips the electronic device as shown in FIG. 6A and FIG. 6B, a state in which the user touches a fingerprint recognizing unit of the electronic device, or a state in which a specific body part of the user or a touch pen is close to a specific part of the electronic device as shown in FIG. 6C. In addition, the sensing condition may be satisfied when the user releases a security lock. When the state of the electronic device is sensed, the electronic device may perform step 420.

In step 420, the electronic device may determine whether the state sensed in step 410 satisfies a predetermined condition. More particularly, the electronic device may determine whether the electronic device is close to the user. As discussed above, the electronic device may determine that it is close to the user when the electronic device detects that it is being gripped and/or touched by the user. Additionally or alternatively, the electronic device may determine that it is close to the user when a particular operation is performed on the device (e.g., a security lock release). When the condition is not satisfied, the process returns to step 410. However, when the state sensed in step 410 satisfies the predetermined condition, the electronic device may perform step 430.

After performing step 430, the electronic device may detect the concentration of the sensed gas, and the like.

Referring to FIG. 5, in step 510, the electronic device may sense its state through the state sensing unit 130. The sensed state may be a state in which the electronic device is positioned within a range previously configured by a user. In addition, the sensed state may be a state in which the electronic device enters into coverage of a higher rank node performing wired and wireless communication with the electronic device. When the state of the electronic device is sensed, the electronic device may perform step 520.

In step 520, the electronic device may determine whether the state sensed in step 510 satisfies a predetermined condition. As discussed above, the predetermined condition may be satisfied when the electronic device is located in a particular area (e.g., a geographic area, a coverage area of a wireless network node, etc.). When the condition is not satisfied, the process returns to step 510. However, when the condition is satisfied, the electronic device may perform step 530.

Next, the electronic device performing step 530 may perform an analysis of the concentration of the sensed gas, and the like.

FIG. 4 may be an operation example for measuring the concentration of the gas distributed in a narrow range, and FIG. 5 may an operation example of the electronic device for measuring the concentration of the gas distributed in a wide range.

Figure 7:
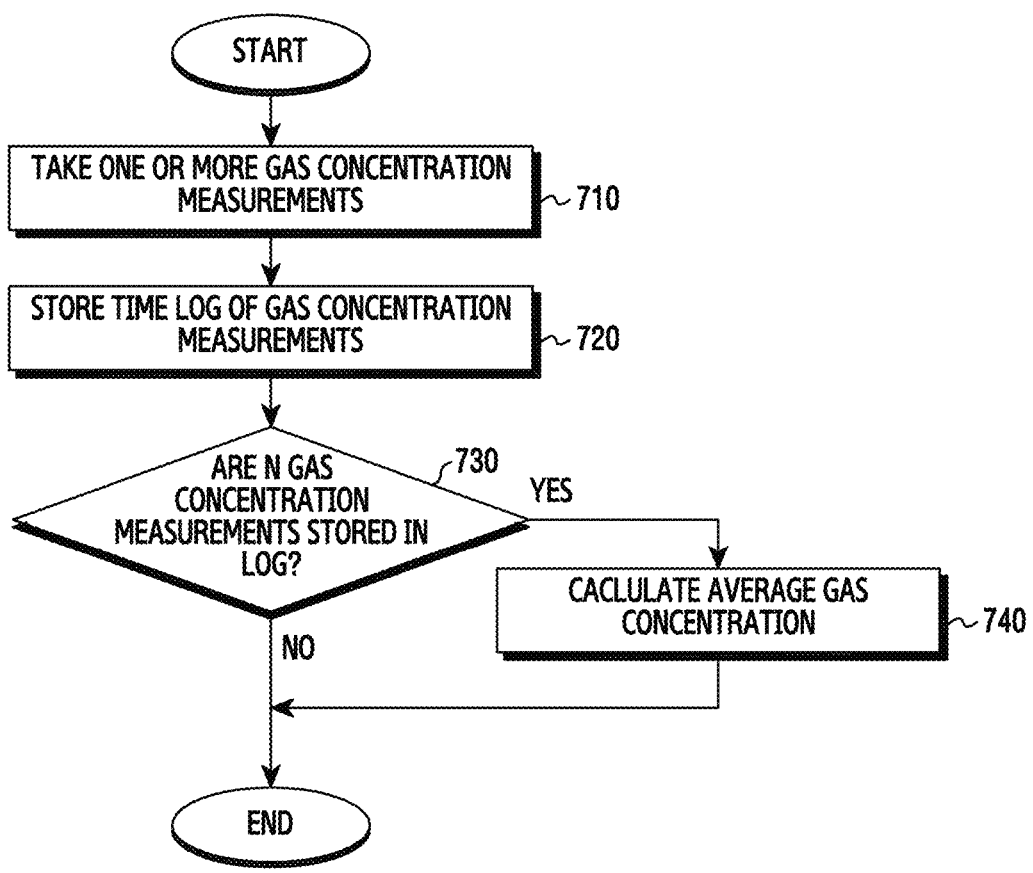
FIG. 7 is a flowchart of an example of a process, according to various embodiments of the present disclosure.

FIG. 7 is a flowchart of an example of a process, according to various embodiments of the present disclosure. According to the process, when the gas is sensed in step 330, 430 or 530, the electronic device may obtain gas concentration data in step 710. The concentration data may include one or more concentration measurements.

The electronic device may then store the concentration data in a time log that is present in the memory 150 in step 720. The time log may identify one or more concentration measurements, as well as the respective time at which each of the measurements is taken. Step 720 may be an operation for storing the log data for analyzing an average concentration of the gas optimized to a user. The electronic device may measure a time when the concentration of the gas registered by the user is the highest through the concentration data stored in step 720, and may draw the gas use cycle of the user.

When the concentration data is stored in a time log in step 720, the electronic device may detect the amount of available concentration data. More particularly, the electronic device may determine whether the available concentration data includes a threshold number of concentration measurements (e.g., N measurements, wherein N is a positive integer). According to aspects of the disclosure, step 720 may be performed because the average concentration data may be unreliable data if the average concentration is measured in a state in which the concentration data stored in the time log is too low. If the concentration data does not include the threshold number of measurements, the process ends. However, if the concentration data includes the threshold number of measurements, the process proceeds to step 740.

In step 740, the electronic device may calculate the average concentration for a given time period (e.g., when N measurements captured during the time period are part of the concentration data). The average concentration measured in step 740 may be used as a reference concentration when the display unit 140 performs a display operation. In addition, the average concentration measured in step 740 may be the concentration data of the gas optimized to the user. In addition, the average concentration measured in step 740 may be data for measuring the average concentration change amount per time. The electronic device may specify a time point when the electronic device displays the gas release message, using the average concentration change amount per time.

Figure 8:
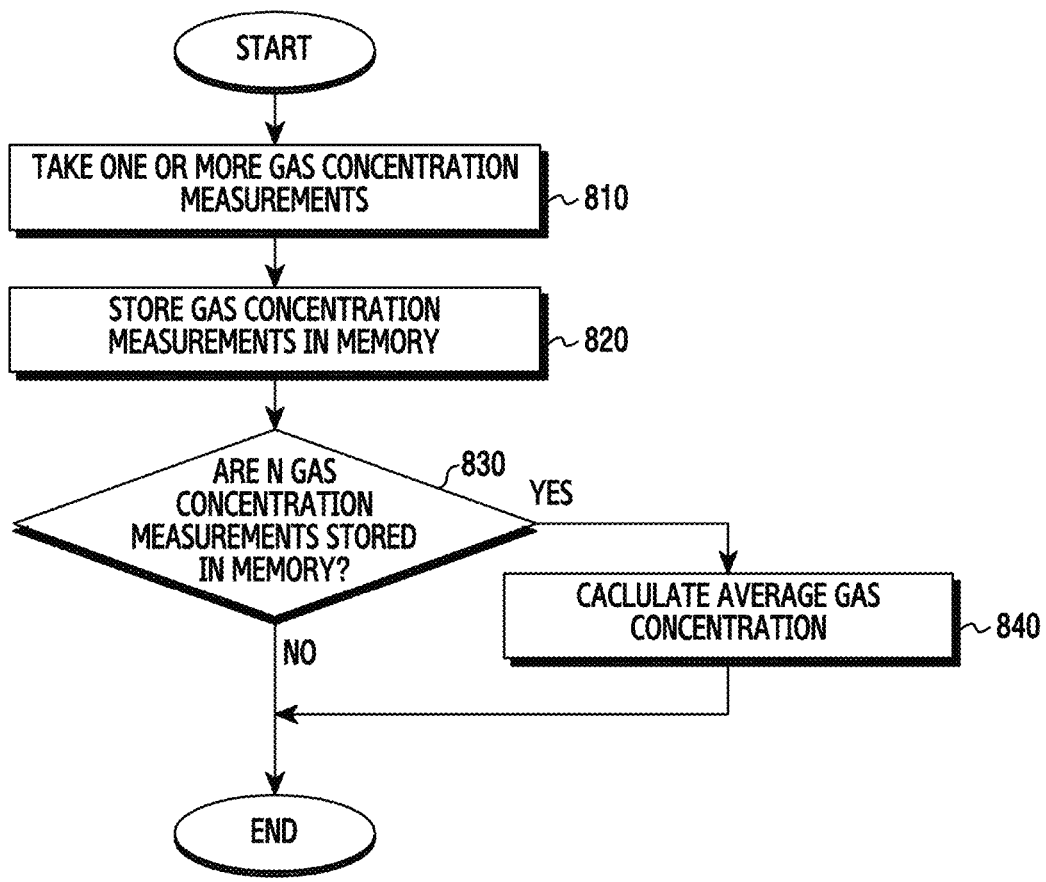
FIG. 8 is a flowchart of an example of a process, according to various embodiments of the present disclosure.

FIG. 8 is a flowchart of an example of a process, according to various embodiments of the present disclosure. According to the process, when the gas is sensed in step 330, 430 or 530, the electronic device may obtain gas concentration data in step 810. The gas concentration data may include one or more gas concentration measurements.

After analyzing the concentration of the gas in step 810, the electronic device may store the concentration data for the detected concentration in step 820. In step 820, the electronic device may not store concentration data based on time and may store the concentration data differently from step 720. This is because there may be an environment in which the division of the concentration data according to time is meaningless according to a measurement environment. When the concentration data is stored in step 820, the electronic device may determine, in step 830, whether the concentration data includes a threshold number of measurements (e.g., N measurements, wherein N is a positive integer). If the concentration data does not include the threshold number of measurements, the process ends. Otherwise, if the concentration data includes the threshold number of measurements, the process proceeds to step 840.

In step 840, the electronic device may calculate average concentration. In the above example, the electronic device may measure an average concentration of a specific gas through step 840. In addition, the average concentration of the specific gas may be a value that should absolutely be maintained regardless of the lapse of time. Therefore, when the concentration of the sensed gas is lower than the average concentration of the specific gas, the electronic device may display the gas release message through the display unit 140. Here, the specific gas may be a gas forming the main ingredient of a scent. For example, in the case of a perfume, the specific gas may be at least one gas that is the main ingredient of the corresponding perfume.

Figure 9:
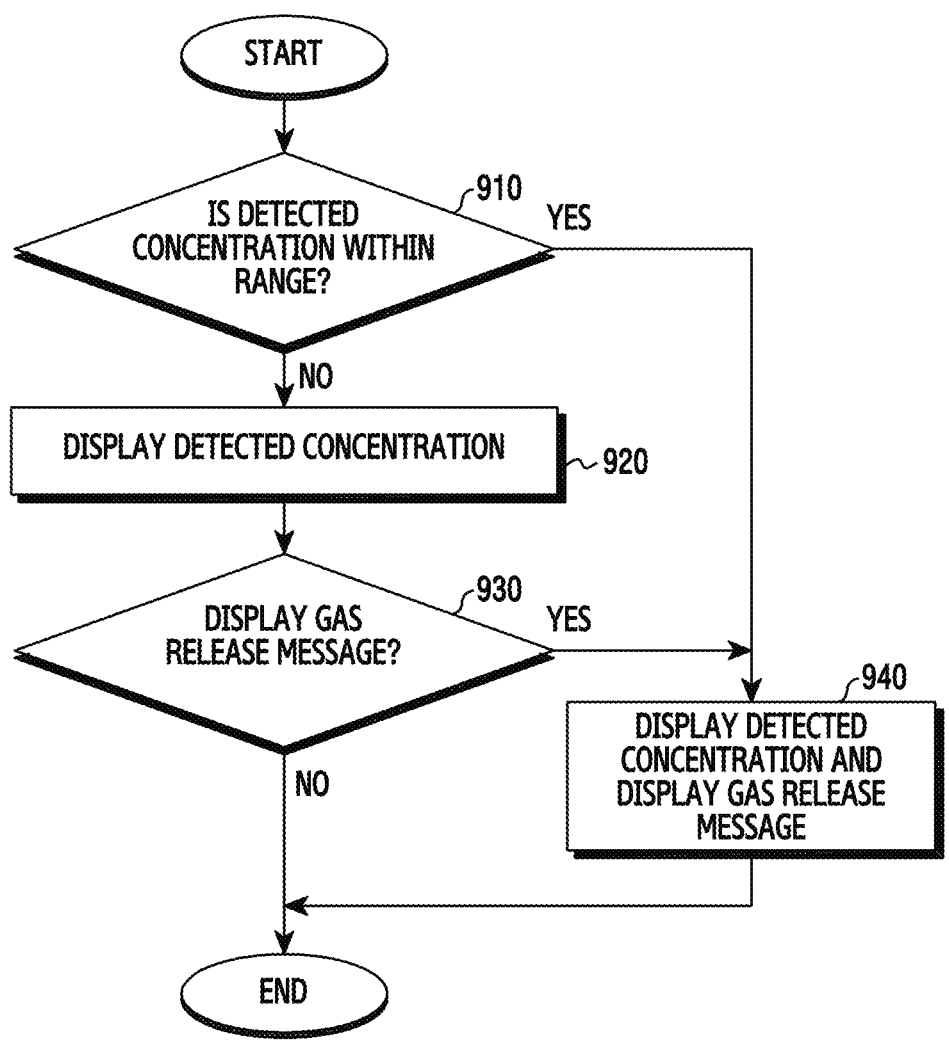
FIG. 9 is a flowchart of an example of a process, according to various embodiments of the present disclosure.

FIG. 9 is a flowchart of an example of a process, according to various embodiments of the present disclosure. According to the process, in step 910, the electronic device may determine whether the detected concentration is within a predetermined range.

When the detected concentration is within the predetermined range (e.g., reference range), in step 920, the electronic device may display the detected concentration. In contrast, when the detected concentration is out of the predetermined range, in step 940, the electronic device may display the detected concentration, and may display the gas release message. For example, the condition for determining the reference range may be based on an upper limit value or a lower limit value. For example, in a case in which the gas should be maintained at a concentration equal to or more than a constant concentration, like a perfume, an air freshener product, and the like, the electronic device may configure a lower limit value of the reference range, and when the concentration of the gas is decreased to a value lower than the lower limit value, the electronic device may generate and display the gas release message. In addition, in the case of sensing a dangerous gas, like a gas range, and the like, the electronic device may configure an upper limit value of the reference range, and when the concentration of the gas is sensed in a value equal to or more than the upper limit value, the electronic device may generate and display the gas release message. A method of displaying the gas release message may correspond to the method in step 370.

The method of displaying the detected concentration may be a method displaying an absolute amount of the concentration detected in step 340, 710 or 810. In addition, the method of displaying the detected concentration may be a method displaying a comparative concentration based on the concentration measured in step 740 or 840.

After the electronic device displays the concentration in step 920, the electronic device may determine whether the gas release message display time has arrived in step 930. Step 930 may be an operation related to the gas use cycle of the user. When the average gas concentration is specified through step 740, the electronic device may measure the average gas change amount per time in step 930. In addition, when the measured average gas change amount per time is used, a time when the gas is out of the range may be expected. When the gas release (e.g., supplement or charge) time arrives according to the expectation in step 940, the electronic device may display the gas concentration and the gas release message. A method of displaying the gas release message may correspond to the method of step 370.

Figure 10:
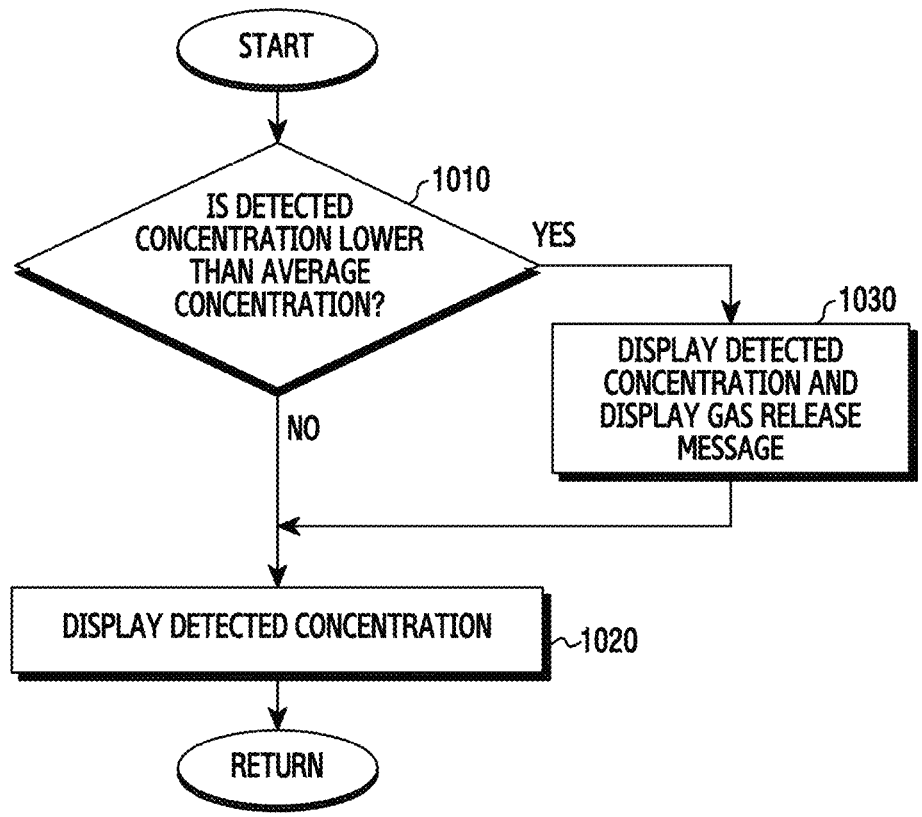
FIG. 10 is a flowchart of an example of a process, according to various embodiments of the present disclosure.

FIG. 10 is a flowchart of an example of a process, according to various embodiments of the present disclosure. According to the process, in step 1010, the electronic device may determine whether a detected concentration is lower than an average concentration. The average concentration may be the average concentration measured through step 840.

When the detected concentration is not lower than the average concentration, in step 1020, the electronic device may display the detected concentration on the display unit 140. In contrast, when the detected concentration is lower than the average concentration, in step 1030, the electronic device may display the detected concentration and a gas release message.

Figure 11:
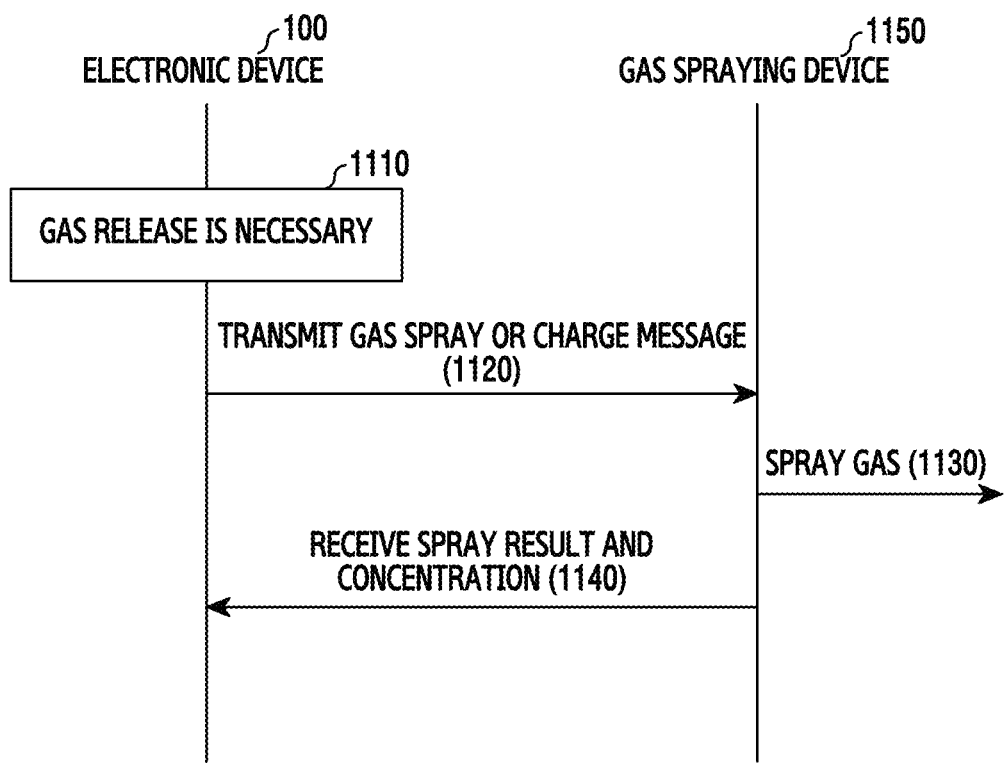
FIG. 11 is a sequence diagram of an example of a process, according to various embodiments of the present disclosure.

FIG. 11 is a sequence diagram of an example of a process which a gas spraying device may communicate with the electronic device, according to various embodiments of the present disclosure. According to the process, the electronic device 100 may sense the gas in a predetermined condition and may detect a concentration of the sensed gas, as shown in FIG. 3. In addition, the electronic device may detect the concentration of the gas, and when the detected concentration of the gas is out of a predetermined range, the electronic device may display a gas release message on the display unit 140. In a case wherein the electronic device includes the gas spraying unit 180, when the electronic device outputs the gas release message as described above, the electronic device may spray the gas by driving the gas spraying unit 180.

In addition, in a case wherein the electronic device may communicate with an external gas spraying device through the communication unit 160, when the electronic device displays the gas release message on the display unit 140, the electronic device may determine whether a gas release is necessary in step 1110. Therefore, in step 1120, the electronic device may transmit a gas release message (e.g., a gas spray message or a gas charge message) to a gas spraying device 1150 through the communication unit 160. Thus, in step 1130, the gas spraying device 1150 may spray the gas, and in step 1140, the gas spraying device 1150 may transmit a spray result and a concentration to the electronic device. Therefore, in step 1140, the electronic device may receive the spray result and the concentration, and may utilize the spray result and the concentration as data for a gas release later.

Figure 12:
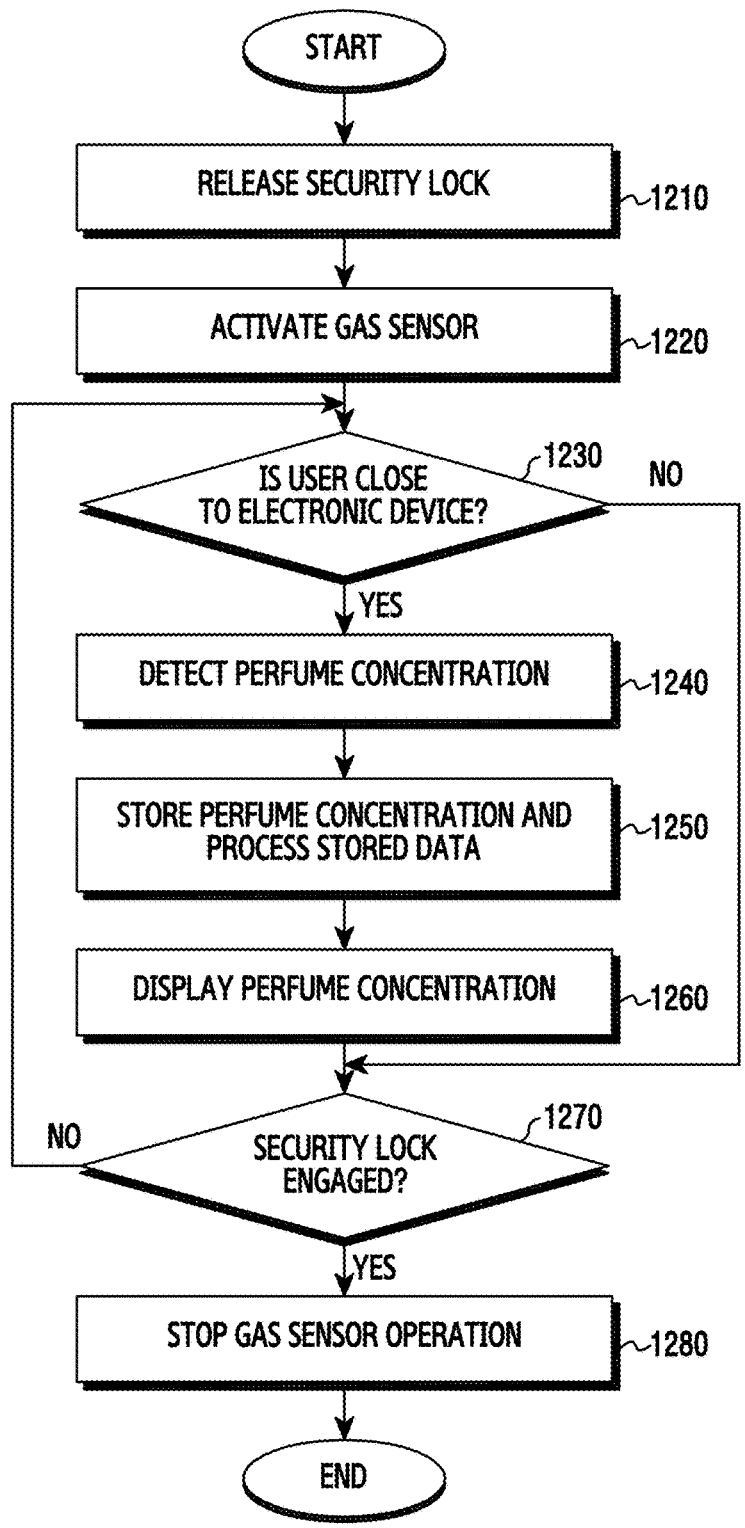
FIG. 12 is a flowchart of an example of a process, according to various embodiments of the present disclosure.

FIG. 12 which a gas spraying device may communicate with the electronic device. According to the process, the electronic device may sense a gas in real time. The electronic device may always drive the gas sensor 110 in a state in which a security lock is released. Therefore, in step 1210, when the electronic device senses the release of the security lock by a user, in step 1220, the electronic device may activate (e.g., drive) the gas sensor 110. In step 1210 in FIG. 12, the security lock release is the example, but step 1210 may be replaced with other operations releasing a sleep state of the electronic device. When the gas sensor 110 is activated, in step 1230, the electronic device may determine whether the electronic device is close to the user. When the electronic device is not close to the user, the electronic device may perform step 1270.

The proximity may mean a state in which the user contacts the electronic device or a state in which the user accesses to the electronic device close. For example, the electronic device may include a grip sensor, the input unit 120 of a touch sensor, a fingerprint recognizing sensor, an illuminance sensor and the like, and when the user is sensed by these sensors, the electronic device may determine that the user is close to the electronic device. When the electronic device is close to the user, in step 1240, the electronic device may detect a perfume concentration. Next, in step 1250, the electronic device may store the perfume concentration. In addition, in step 1250, the electronic device may process the stored perfume concentration. In addition, in step 1260, the electronic device may display the perfume concentration. When the electronic device displays the concentration, in the case of a standby mode, the electronic device may display the gas concentration on a background screen, and in the case of an operation mode, the electronic device may display the gas concentration on an indicator screen.

In step 1270, the electronic device may determine whether the security lock is engaged. When the security lock release state of the electronic device is maintained, the electronic device may perform step 1230 and may continuously determine whether the user is close to the electronic device. Alternatively, when the security lock is performed, in step 1280, the electronic device may turn off the gas sensor operation. The case in which the security lock is performed may be a state in which the user does not use the electronic device. In this case, the user may be disposed in a position far from the electronic device. In addition, in such a state, the electronic device may not sense the gas related to the user, and thus performing the operation of sensing the gas may be a meaningless operation. Therefore, when the security lock state is sensed in step 1270, the electronic device may deactivate (e.g., turn off) the gas sensor 110 in step 1280. Thus, the electronic device may reduce its electric consumption. However, a case that is not a method measuring a specific gas related to the user in a proximity state, or a case in which the gas sensing is necessary in the security lock state, steps 1210, 1270 and 1280 may be omitted.

FIGS. 13A-E are diagrams of examples of different user interfaces. According to aspects of the disclosure, the screens depicted in FIGS. 13A-E may be displayed sequentially with the passage of time. Any of the screens shown in FIGS. 13A-E may be a wallpaper, a home screen, and or any other suitable type of screen.

An indication 1300 shown in FIG. 13A, FIG. 13B, FIG. 13C, FIG. 13D, and FIG. 13E. is shaped as a wave, such that the height (e.g., amplitude) of the wave indicates the concentration of the perfume. The gas sensor 110 of the electronic device may not always be operated as in the embodiment discussed with respect to FIG. 12. However, since the electronic device may store the log data as described above, the electronic device may estimate a current perfume concentration of the user, even though the electronic device does not sense the concentration of the perfume in real time. Thus, screens 1310 to 1350 may be screens showing the current time, or may be screens showing a time when the concentration of the perfume is sensed.

Figure 13A:
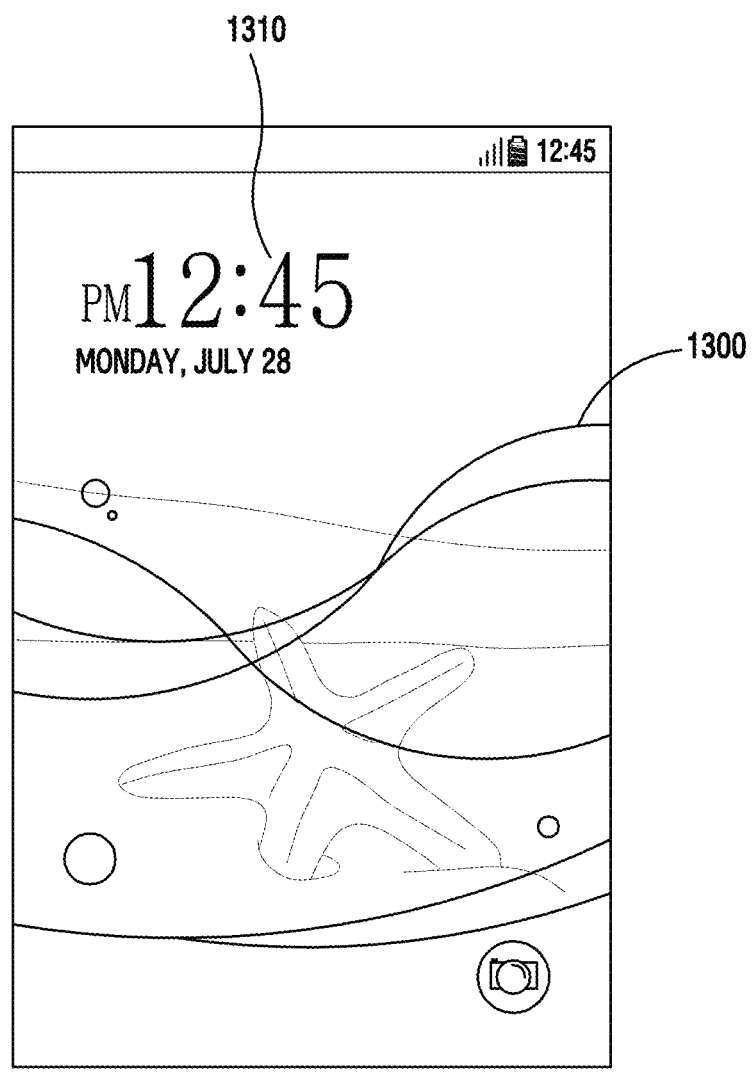
FIG. 13A is a diagram of an example of a user interface, according to various embodiments of the present disclosure.
Figure 13B:
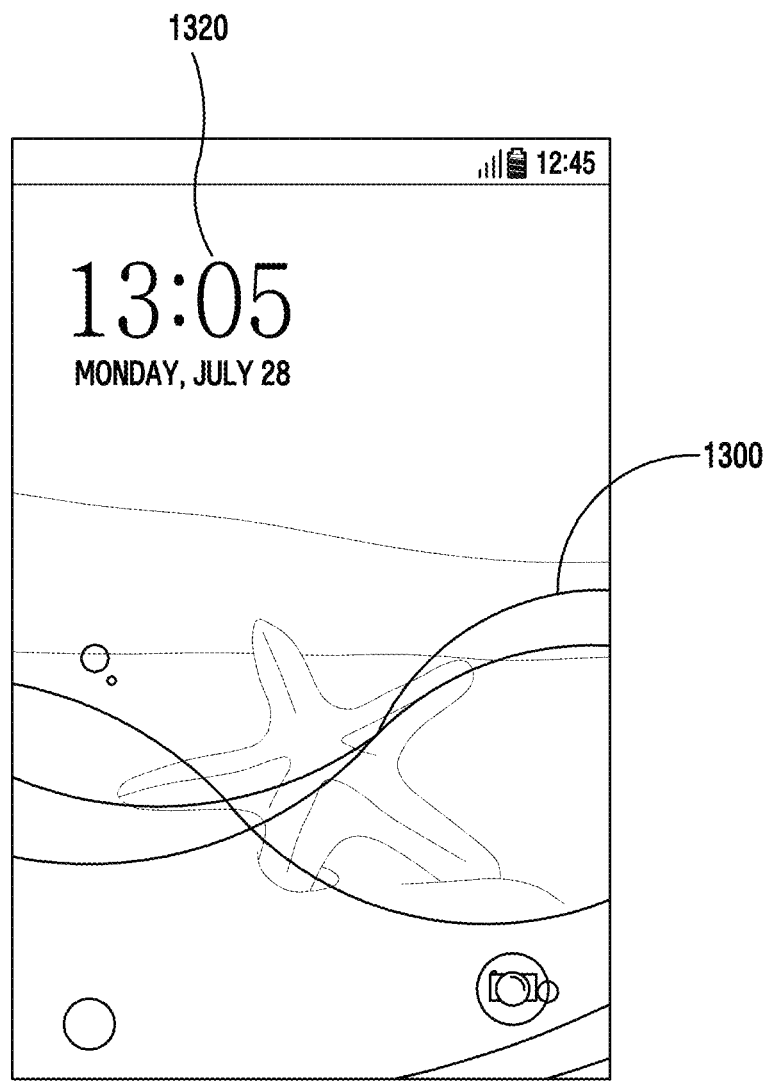
FIG. 13B is a diagram of an example of a user interface, according to various embodiments of the present disclosure.
Figure 13C:
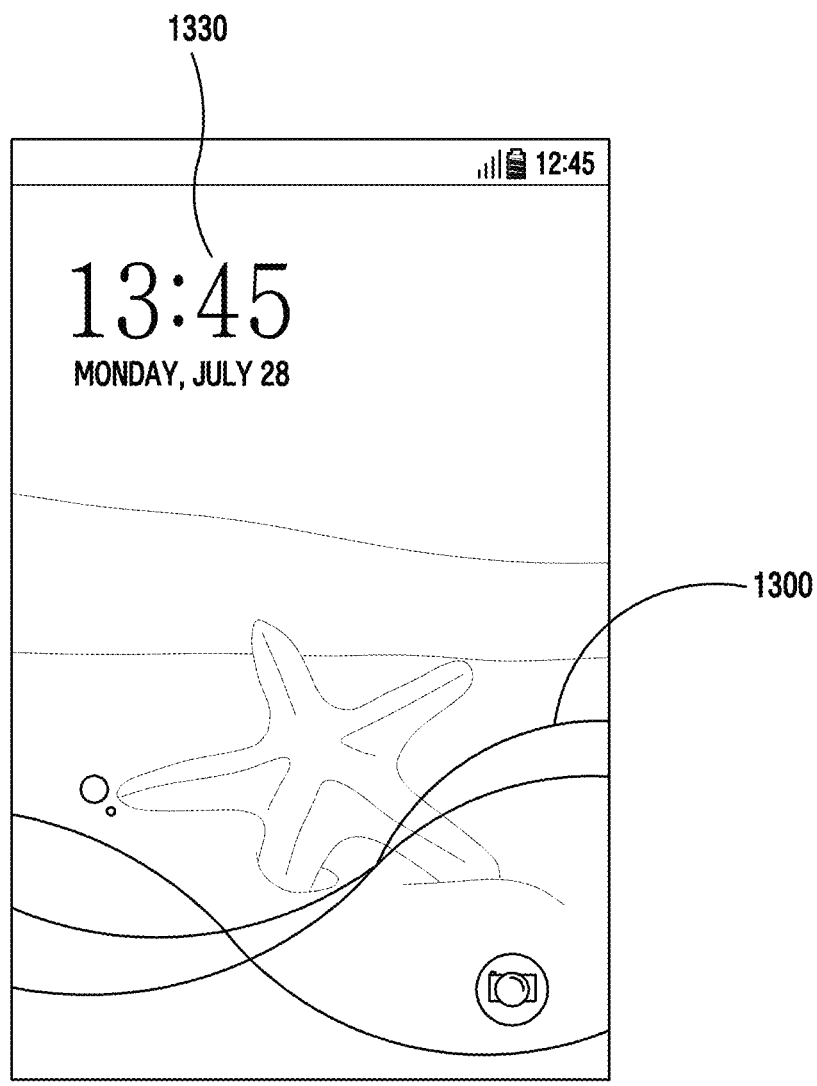
FIG. 13C is a diagram of an example of a user interface, according to various embodiments of the present disclosure.
Figure 13D:
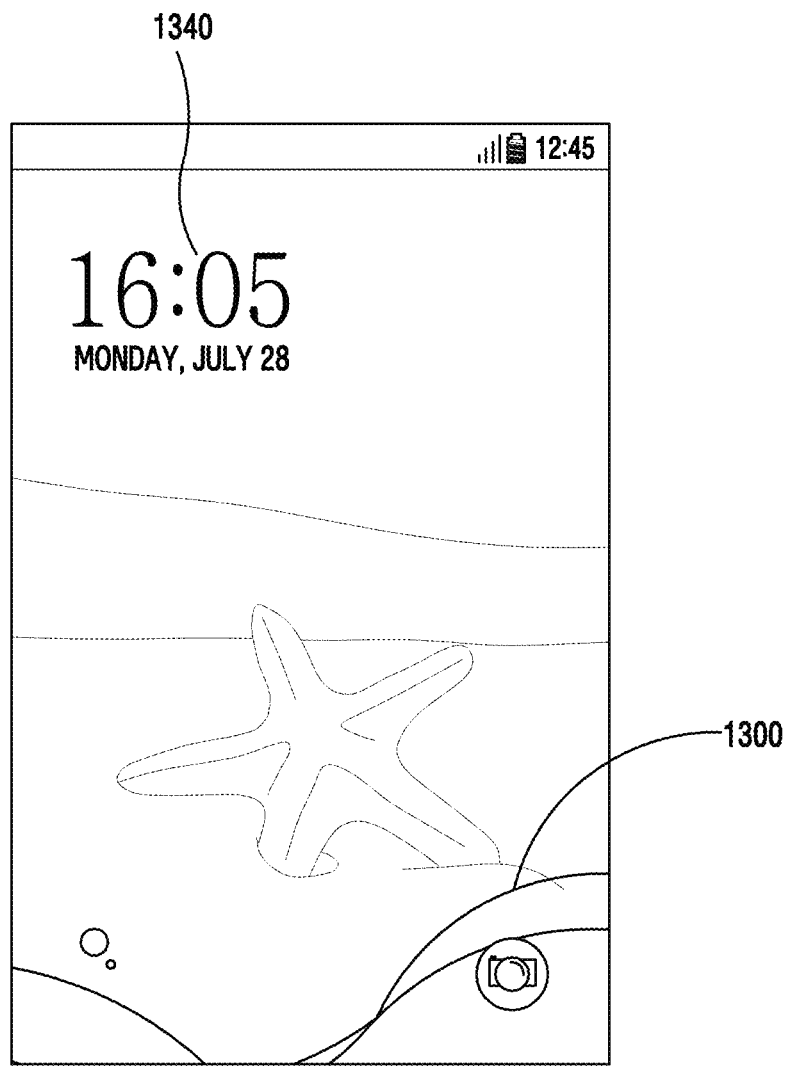
FIG. 13D is a diagram of an example of a user interface, according to various embodiments of the present disclosure.
Figure 13E:
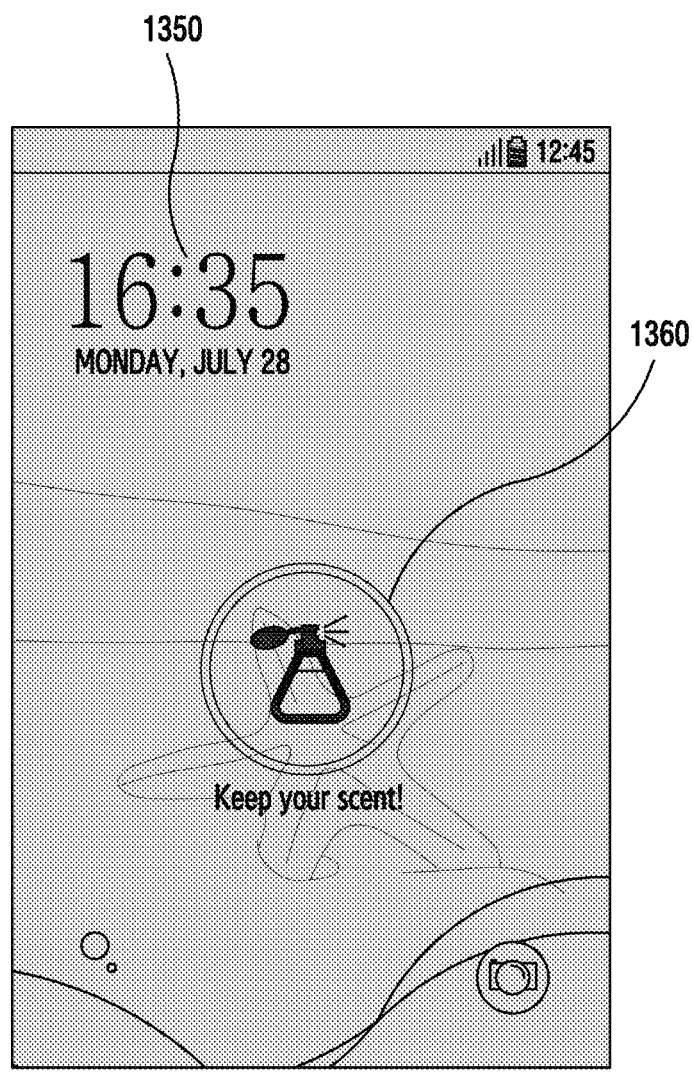
FIG. 13E is a diagram of an example of a user interface, according to various embodiments of the present disclosure.

As shown in FIG. 13E, in order to signal that a supplemental amount of perfume (or another gas) has been released, the electronic device may process the screen such that the screen is darker than usual. In addition, as shown in FIG. 13E, the electronic device may display a screen 1360 that additional perfume is released into the air.

Figure 14A:
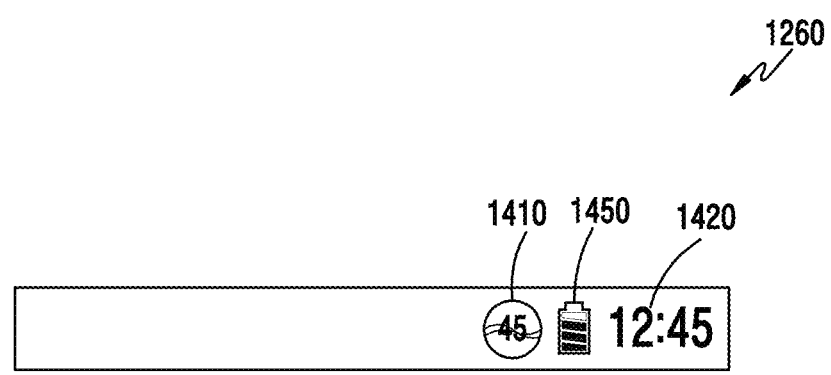
FIG. 14A is a diagram of an example of a user interface, according to various embodiments of the present disclosure.
Figure 14B:
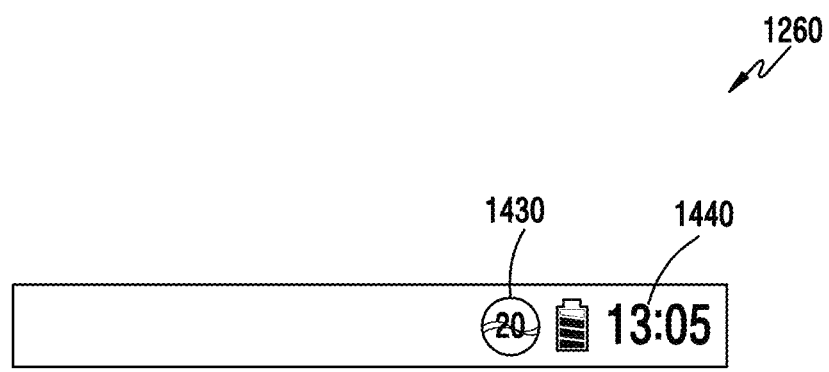
FIG. 14B is a diagram of an example of a user interface, according to various embodiments of the present disclosure.

FIGS. 14A and 14B are diagrams of examples of user interfaces, according to various embodiments of the present disclosure. Referring to FIGS. 14A and 14B, the electronic device displays the detected concentration of the gas on an indicator in real time. The indicator displays the gas concentration 45 in the state 1410 of FIG. 14A, and displays the time in a state 1420. In addition, the indicator displays the gas concentration 20 in the state 1430 of FIG. 14B, and displays the time in the state 1440. The gas concentration 45 or 20 shown in the state 1410 or 1430 may be an absolute value of the detected gas concentration, or may be a relative value based on the average concentration for a given time period. The time shown in the state 1420 or 1440 may be a time when the gas concentration is measured, or may be a current time. The electronic device displays the amount of battery power in the state 1450, and the electronic device may control an operation time of the gas sensor 110 according to the power amount of the battery.

A method of operating an electronic device according to various embodiments of the present disclosure may include sensing a state of the electronic device, sensing a gas if the sensed state is a predetermined condition, analyzing a concentration of the sensed gas, and displaying the detected concentration of the gas.

The displaying may further include displaying a message that informs of a supplement of the gas if the detected concentration of the gas is out of a predetermined range. In addition, the displaying may include displaying the concentration on a standby screen if the electronic device is in a standby mode. In addition, the displaying may include displaying the concentration on an indicator screen if the electronic device is in an active mode.

Also, the method of operating the electronic device may further include storing concentration data corresponding to the detected concentration, calculating an average concentration using concentration measurements that are part of the stored concentration data, if the number of the concentration measurements that are part of the stored concentration data is equal to or larger than a configured reference number, and displaying the detected gas concentration corresponding to the average concentration.

In addition, the storing may include storing the concentration data according to time, and the measuring may include measuring the average concentration for a given time period by using the concentration data, if the number of the concentration measurements stored in a time log is equal to or larger than the reference number. The predetermined condition in the state of the electronic device may be a case in which the electronic device is close to a user or the electronic device makes contact with the user. In this case, the gas sensed by the electronic device may be a perfume. In addition, the predetermined condition in the state of the electronic device may be a case in which the electronic device moves to a configured position.

In addition, the method of operating the electronic device may further include driving a gas sensor if a security lock is released, and turning off the gas sensor if the security lock is operated.

Methods stated in claims and/or specifications according to various embodiments may be implemented by hardware, software, or a combination of hardware and software.

In the implementation of software, a computer-readable storage medium for storing one or more programs (software modules) may be provided. The one or more programs stored in the computer-readable storage medium may be configured for execution by one or more processors within the electronic device. The at least one program may include instructions that cause the electronic device to perform the methods according to various embodiments of the present disclosure as defined by the appended claims and/or disclosed herein.

In addition, the programs may be stored in an attachable storage device which may access the electronic device through communication networks such as the Internet, Intranet, Local Area Network (LAN), Wide LAN (WLAN), and Storage Area Network (SAN) or a combination thereof. Such a storage device may access the electronic device via an external port. Further, a separate storage device on the communication network may access a portable electronic device.

FIGS. 1-14B are provided as an example only. At least some of the operations discussed with respect to these figures can be performed concurrently, performed in different order, and/or altogether omitted. It will be understood that the provision of the examples described herein, as well as clauses phrased as "such as," "e.g.", "including", "in some aspects," "in some implementations," and the like should not be interpreted as limiting the claimed subject matter to the specific examples.

The above-described aspects of the present disclosure can be implemented in hardware, firmware or via the execution of software or computer code that can be stored in a recording medium such as a CD-ROM, a Digital Versatile Disc (DVD), a magnetic tape, a RAM, a floppy disk, a hard disk, or a magneto-optical disk or computer code downloaded over a network originally stored on a remote recording medium or a non-transitory machine-readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. Any of the functions and steps provided in the Figures may be implemented in hardware, software or a combination of both and may be performed in whole or in part within the programmed instructions of a computer. No claim element herein is to be construed under the provisions of 35 U.S.C. 112, sixth paragraph, unless the element is expressly recited using the phrase "means for". The terms "unit" or "module" referred to herein is to be understood as comprising hardware such as a processor or microprocessor configured for a certain desired functionality, or a non-transitory medium comprising machine executable code, in accordance with statutory subject matter under 35 U.S.C. §101 and does not constitute software per se.

Moreover, the embodiments disclosed in this specification are suggested for the description and understanding of technical content but do not limit the range of the present disclosure. Accordingly, the range of the present disclosure should be interpreted as including all modifications or various other embodiments based on the technical idea of the present disclosure.

What is claimed is:

1. A method for use in an electronic device, comprising:
sensing a state of the electronic device;
determining whether the state satisfies a designated condition;
determining, in response to determining that the state satisfies the designated condition, a concentration of a gas detected via a gas sensor of the electronic device; and
displaying an indication of the concentration of the gas, wherein the displaying the indication comprises displaying, in response to identifying that the concentration of the gas is out of a designated range, a message for indicating that additional gas is required, with the indication.

2. The method of claim 1, wherein the indication of the concentration of the gas is displayed on a standby screen if the electronic device is in a standby mode.

3. The method of claim 1, wherein the indication of the concentration of the gas is displayed on an indicator screen if the electronic device is in an active mode.

4. The method of claim 1, further comprising:
perform a plurality of gas concentration measurements; and
determining, based on a result of the plurality of gas concentration measurements, an average gas concentration if a count of the plurality of gas concentration measurements is equal to or larger than a reference number.

5. The method of claim 4, wherein the average concentration is calculated for a given time period, and the average gas concentration is calculated in response to identifying that a count of the plurality of gas concentration measurements performed during the given time period is equal to or larger than the reference number.

6. The method of claim 1, wherein the designated condition is satisfied when the electronic device is held by a user or when the user interacts with the electronic device.

7. The method of claim 1, wherein the designated condition is satisfied when the electronic device is located within a designated area.

8. The method of claim 1, further comprising:
activating the gas sensor in response to a security lock of the electronic device being released; and
deactivating the gas sensor in response to the security lock being engaged.

9. The method of claim 1, wherein the gas includes a perfume.

10. An electronic device comprising:
a memory storing instructions;
a display; a
a gas sensor; and
at least one processor, operatively coupled to the memory, configured to execute the stored instructions to:
sense a state of the electronic device;
determine whether the state satisfies a designated condition;
determine, in response to determining that the state satisfies the designated condition, a concentration of a gas detected via the gas sensor; and
display an indication of the concentration of the gas on the display,
wherein the at least one processor is further configured to execute the stored instructions to display, in response to identifying that the concentration of the gas is out of a designated range, a message for indicating that additional gas is required, with the indication.

11. The electronic device of claim 10, wherein the indication of the concentration of the gas is displayed on a standby screen if the electronic device is in a standby mode.

12. The electronic device of claim 10, wherein the indication of the concentration of the gas is displayed on an indicator screen if the electronic device is in an active mode.

13. The electronic device of claim 10, wherein the at least one processor is further configured to execute the stored instructions to:
perform a plurality of gas concentration measurements; and
determine, based on a result of the plurality of gas concentration measurements, an average gas concentration if a count of the plurality of gas concentration measurements is equal to or larger than a reference number.

14. The electronic device of claim 13, wherein the average concentration is calculated for a given time period, and the average gas concentration is calculated in response to identifying that a count of the plurality of gas concentration measurements performed during the given time period is equal to or larger than the reference number.

15. The electronic device of claim 10, wherein the designated condition is satisfied when the electronic device is held by a user or when the user interacts with the electronic device.

16. The electronic device of claim 10, wherein the designated condition is satisfied when the electronic device is located within a designated area.

17. The electronic device of claim 10, wherein the at least one processor is further configured to execute the stored instructions to:
activate the gas sensor in response to a security lock of the electronic device being released; and
deactivate the gas sensor in response to the security lock being engaged.

18. The electronic device of claim 10, wherein the gas includes a perfume.

* * * * *